US010441161B2

(12) United States Patent
Padula et al.

(10) Patent No.: US 10,441,161 B2
(45) Date of Patent: Oct. 15, 2019

(54) HOLOGRAPHIC REAL SPACE REFRACTIVE SEQUENCE

(71) Applicant: Veyezer LLC, Killingworth, CT (US)

(72) Inventors: William V. Padula, Killingworth, CT (US); Teddi R. Dinsmore, Killingworth, CT (US)

(73) Assignee: Veyezer LLC, Killingworth, CT (US)

( * ) Notice: Subject to any disclaimer, the term of this patent is extended or adjusted under 35 U.S.C. 154(b) by 38 days.

(21) Appl. No.: 15/904,995

(22) Filed: Feb. 26, 2018

(65) Prior Publication Data

US 2019/0261847 A1   Aug. 29, 2019

(51) Int. Cl.
| | |
|---|---|
| *A61B 3/00* | (2006.01) |
| *G06T 19/00* | (2011.01) |
| *A61B 3/028* | (2006.01) |
| *A61B 3/036* | (2006.01) |
| *A61B 3/08* | (2006.01) |

(52) U.S. Cl.
CPC ............ *A61B 3/005* (2013.01); *A61B 3/0033* (2013.01); *A61B 3/028* (2013.01); *G06T 19/003* (2013.01); *A61B 3/036* (2013.01); *A61B 3/08* (2013.01)

(58) Field of Classification Search
CPC ....... A61B 3/005; A61B 3/028; A61B 3/0033; A61B 3/08; A61B 3/036; G06T 19/003
USPC ........................................ 351/220, 222, 223
See application file for complete search history.

(56) References Cited

U.S. PATENT DOCUMENTS

| 5,491,492 A | 2/1996 | Knapp et al. |
| 9,101,312 B2 | 8/2015 | Waldorf et al. |
| 2016/0270656 A1* | 9/2016 | Samec ................ A61B 3/085 |

FOREIGN PATENT DOCUMENTS

| CN | 105662334 B | 7/2017 |
| DE | 3405778 A1 | 8/1985 |

OTHER PUBLICATIONS

Vision Testing with a Hologram, Eye Focus, published Jan. 2011, http://www.eyefocus.com.au/common/node/10.
Avudainayagam et al., A Test for Progressive Myopia and the Role of Latent Accommodation in its Development, International Journal of Ophthalmology and Clinical Research, 2015, 2:2, published Apr. 10, 2015.

* cited by examiner

*Primary Examiner* — Tuyen Tra
(74) *Attorney, Agent, or Firm* — McCarter & English, LLP

(57) ABSTRACT

A system and a method for holographic refraction eye testing device is disclosed. The system renders one or more three dimensional objects within the holographic display device. The system updates the rendering of the one or more three dimensional objects within the holographic display device, by virtual movement of the one or more three dimensional objects within the level of depth. The system receives input from a user indicating alignment of the one or more three dimensional objects after the virtual movement. The system determines a delta between a relative virtual position of the one or more three dimensional objects at the moment of receiving input and an optimal virtual position and generates prescriptive remedy based on the delta.

20 Claims, 8 Drawing Sheets

HOLOGRAPHIC REAL SPACE REFRACTIVE SEQUENCE

BACKGROUND

1. Technical Field

Systems and methods for providing a visual examination using holographic projection in real space and time are provided.

2. Background Art

For over one hundred years doctors have provided eye examinations including refraction by using lenses and prisms to determine the refractive state and binocularity of the patient. Refraction means to bend light. Persons with myopia (nearsightedness), hyperopia (farsightedness) and astigmatism (two different power curves) performed a refraction to correct the refractive state and blurred vision of the patient by using physical lenses and prisms. While in the 19th century the refraction was mostly conducted with a trial frame by holding up individual lenses before each eye to make the image more clear, in the 20th century the phoropter (meaning "many lenses") was developed. This instrument was extended on the arm of a physical stand and the instrument was positioned before the patient's face. The clinician would then turn the dial to move different lenses in front of the person's eyes to find the best subjective refraction to improve distance vision. The instrument was then advanced to include prisms that could be used to disassociate images or change the position of the image enabling the clinician the ability to evaluate muscle ranges and the ability to maintain eye alignment and binocularity. It also permitted assessment of the person's ability to accommodate or focus at a near range. This was all for the purpose of designing glasses to improve eyesight and visual acuity for both distance and near ranges as well as to prescribe prisms to correct for imbalance in eye alignment affecting binocularity.

While the phoropter is an effective instrument and still used today, it limits the peripheral field and cannot assess binocularity in any other meridian other than primary gaze or looking straight ahead. Binocular imbalances can sometimes only be represented with gaze outside of the primary gaze position. Therefore, the instrument has limited value for these purposes and/or lead the clinician to only be able to prescribe lenses and prisms for one position of the eyes. In addition, the large phoropter blocks the peripheral vision producing an abnormal environment and restriction of side vision, which frequently affects the intensity of the attentional visual process and cause the refractive correction to be too strong or imbalanced.

These and other issues and limitations of existing instruments and technologies are addressed and overcome by the systems and methods of the present disclosure.

SUMMARY OF THE INVENTION

Described herein is a system to evaluate the refractive state of the eye and visual process as well as binocularity in the nine cardinal positions of gaze while in real space by using holographic projection for each eye. The refractive state assessment has been designed to enable the eye of the patient to focus on a three dimensional target in the manner that the refractive imbalance will focus to maintain clear vision. For example, a target is presented with three dimensions. The myopic eye will focus on the near side of the target and see it with clarity. The dimensions and position of the target is then moved to refocus the far or distance side of the target and calibration is determined as to the power of the eye and the power of the lens required to re-focus the eye to best visual acuity at infinity. The same would occur for the hyperopic eye, only the far portion of the three-dimensional target will be in initial focus.

The patient uses hand movements and/or voice command to communicate the subjective measurement of the dioptric power to correct the vision to best visual acuity and, advantageously, these objectives are accomplished through manipulation of the target in real space. More particularly, in an exemplary embodiment of the present disclosure, an eye with astigmatism would be presented a three dimensional object where perpendicular lines would enable the patient to observe that one of the lines is clear and the other blurred. The target will be rotated to determine the axis of the astigmatism and then the opposite or blurred side of the target would be shifted in space virtually to bring it into focus. This sequence of operation will provide the amount of astigmatism measured in this eye and therefore the predicted amount of cylindrical correction needed to bring clarity. If the patient has both myopia or hyperopia and astigmatism, the target would be simultaneously be manipulated to determine myopia or hyperopia while also evaluation the dioptric power of the astigmatism.

Additional features, functions and benefits of the disclosed systems and methods will be apparent from the detailed description which follows, particularly when read in conjunction with the accompanying figures.

BRIEF DESCRIPTION OF DRAWINGS

Illustrative embodiments are shown by way of example in the accompanying drawings and should not be considered as a limitation of the present disclosure.

DETAILED DESCRIPTION

Apparatus, methods, and non-transitory computer readable medium are described for a holographic refraction eye testing device. Example embodiments provide a device for utilizing holographic virtual projection to perform eye testing, diagnosis, and prescriptive remedy.

In some embodiments, the disclosed holographic eye testing device renders on a head mounted device, one or more three dimensional objects within the holographic display device. wherein the rendering corresponds to a virtual level of depth viewable by a user. The holographic display device updates the rendering of the one or more three dimensional objects, wherein the updates include a virtual movement of the one or more three dimensional objects within the virtual level of depth. The holographic display device receives input from a user, wherein the input includes an indication of alignment of the one or more three dimensional objects based on the virtual movement The indication of alignment includes a relative position between the one or more three dimensional objects. The holographic display device determines a delta between the relative virtual position between the one or more three dimensional objects and an optimal virtual position. The holographic display device generates prescriptive remedy based on the delta.

Figure 1:
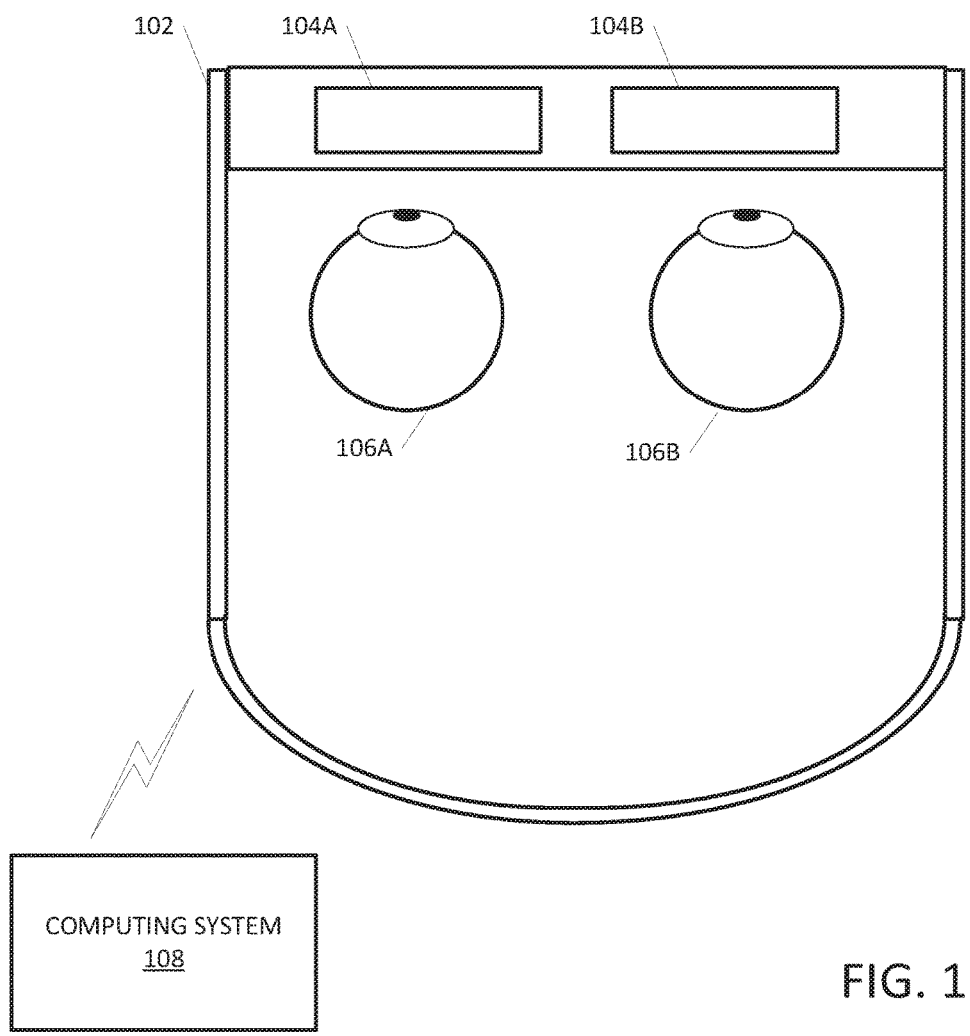
FIG. 1 is a block diagram illustrating a system for the holographic refraction eye testing device according to an exemplary embodiment.

FIG. 1 is a block diagram illustrating a system for the holographic refraction eye testing device according to an exemplary embodiment. In one embodiment, the holographic refraction eye testing device can include a head mounted display (HMD) 102. The HMD 102 can include a pair of combiner lenses 104A, 104B for rendering three dimensional (3D) images within a user's field of view (FOV). The combiner lenses 104A, 104B can be calibrated to the interpupillary distance from the users eyes 106A, 106B. A computing system 108 can be connected to the combiner lenses 104A, 104B. The holographic refraction eye testing device can be repositioned in any of the nine primary gaze positions as needed. These tests are built to run on technical platforms which can project 3D holographic images within a field of view provided by a wired or wireless headset. The HMD 102 can be connected to an adjustable, cushioned inner headband, which can tilt the combiner lenses 104A, 104B up and down, as well as forward and backward. To wear the unit, the user fits the HMD 102 on their head, using an adjustment wheel at the back of the headband to secure it around the crown, supporting and distributing the weight of the unit equally for comfort, before tilting the visor and combiner lenses 104A, 104B towards the front of the eyes.

The computing system 108 can be inclusive to the HMD 102, where the holographic refraction eye testing device is a self contained apparatus. The computing system 108 in the self contained apparatus can include additional power circuitry to provide electrical current to the parts of the computing system 108. Alternatively, the computing system 108 can be external to the HMD 102 and communicatively coupled either through wired or wireless communication channels to the HMD 102. Wired communication channels can include digital video transmission formats including High Definition Multimedia Interface (HDMI), DisplayPort™ (DisplayPort is a trademark of VESA of San Jose Calif., U.S.A.), or any other transmission format capable of propagating a video signal from the computing system 108 to the combiner lenses 104A, 104B. Additionally, the HMD 102 can include speakers or headphones for the presentation of instructional audio to the user during the holographic refraction eye tests. In a wireless communication embodiment, the HMD 102 can include a wireless adapter capable of low latency high bandwidth applications, including but not limited to IEEE 802.11ad. The wireless adapter can interface with the computing system 108 for the transmission of low latency video to be displayed upon the combiner lenses 104, 104B.

Additionally the computing system 108 can including software for the manipulation and rendering of 3D objects within a virtual space. The software can include both platform software to support any fundamental functionality of the HMD 102, such as motion tracking and input functionality. Platform software can be implemented in a virtual reality (VR) framework, augmented reality (AR) framework, or mixed reality (MR) framework. Platform software to support the fundamental functionality can include but are not limited to SteamVR® (SteamVR is a registered trademark of the Valve Corporation, Seattle Wash., U.S.A.) software development kit (SDK), Oculus® VR SDK (Oculus is a registered trademark of Oculus VR LLC, Irvine Calif., U.S.A.), OSVR (Open source VR) (OSVR is a registered trademark of Razer Asia Pacific Pte. Ltd. Singapore) SDK, and Microsoft Windows Mixed Reality Computing Platform. Application software executing on the computing system 108 with the underlying platform software can be a customized rendering engine, or an off-the-shelf 3D rendering framework, such as Unity® Software (Unity Software is a registered trademark of Unity Technologies of San Francisco Calif., U.S.A.). The rendering framework can provide the basic building blocks of the virtualized environment for the holographic refractive eye test, including 3D objects and manipulation techniques to change the appearance of the 3D objects. The rendering framework can provide application programming interfaces (APIs) for the instantiation of 3D objects and well-defined interfaces for the manipulation of the 3D objects within the framework. Common software programming language bindings for rendering frameworks include but are not limited to C++, Java, and C#. Additionally the application software can provide settings to allow a test administrator to adjust actions within the test, such as holographic object speed and object color.

Figure 2:
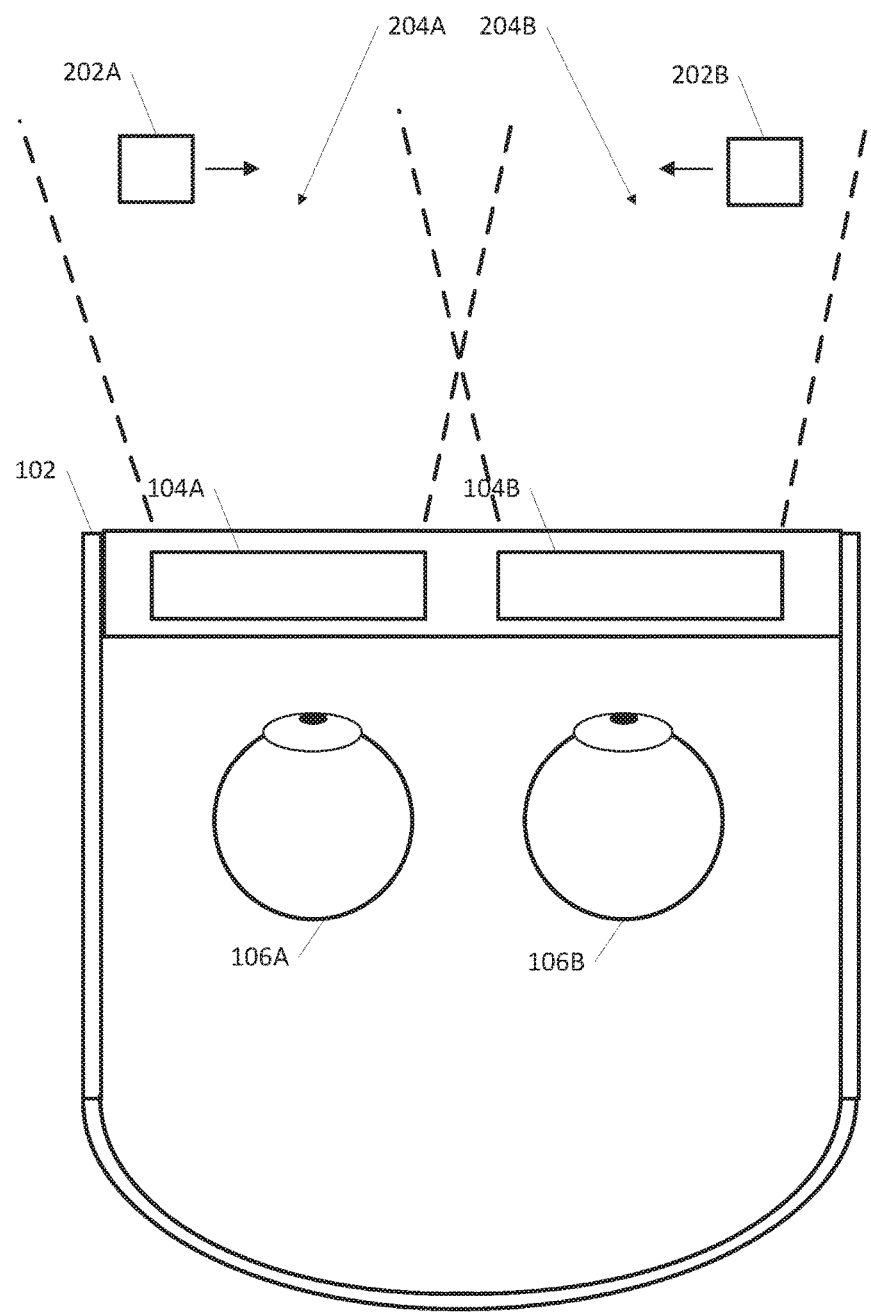
FIG. 2 is a block diagram illustrating a test for horizontal phoria with a holographic refraction eye testing device according to an exemplary embodiment.

FIG. 2 is a block diagram illustrating a test for horizontal phoria with a holographic refraction eye testing device according to an exemplary embodiment. In one embodiment, two virtual 3D objects 202A, 202B can be manipulated in a user's field of view (FOV) 204A, 204B. The virtual 3D objects 202A, 202B can be translated within the same horizontal plane until convergence. The virtual 3D objects 202A, 202B can have a starting point within the user's FOV 204A, 204B equidistant within the same horizontal plane from a mid-point of the FOV. Utilizing application software, the virtual 3D objects 202A, 202B are translated and projected on the combiner lenses 104A, 104B to give the appearance that the virtual 3D objects are a set distance from the view of the user's eyes 106A, 106B. The application software can present the virtual 3D objects 202A, 202B via the combiner lenses 104A, 104B so that the virtual 3D objects can appear to be at different distances from the user's eyes 106A, 106B. In some embodiments the presentation of the virtual 3D objects 202A, 202B can correspond to projection of the virtual 3D objects at distances of 16 inches to 20 feet in front of the user's eyes 106A, 106B. The range of distances allow phoria to be measured at different intervals of depth for better confidence in convergence results. As the virtual 3D objects 202A, 202B approach the mid-point of the user's FOV, the user can provide input to the application software or platform software. The input can take the form of voice commands, gestures, or input from a "clicker." As the virtual 3D objects 202A, 202B approach each other, they will begin to overlap and converge into a single virtual 3D object. At the point in which the convergence becomes clear to the user, the user can provide input to stop any motion or translation of the virtual 3D objects 202A, 202B. The application software evaluates a delta between the midpoint of the user's FOV 204A, 204B and the point at which the virtual 3D objects 202A, 202B were located when the user provided input to stop the motion or translation. The delta can be represented as a deviation relative to the virtual distance of the virtual 3D objects 202A, 202B from the patient. A diopter is measured by the deviation of the image at a specific virtual distance (1 prism diopter=1 virtual cm deviation of the image at a 1 virtual meter distance).

Figure 3:
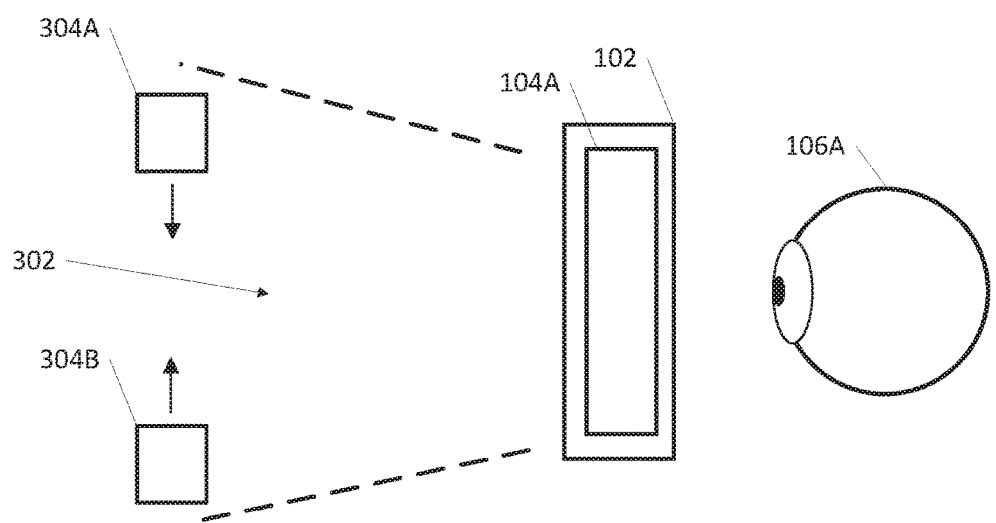
FIG. 3 is a block diagram illustrating a test for vertical phoria utilizing the holographic refraction eye testing device according to an exemplary embodiment.

FIG. 3 is a block diagram illustrating a test for vertical phoria utilizing the holographic refraction eye testing device according to an exemplary embodiment. In one embodiment, two virtual 3D objects 304A, 304B can be manipulated in a user's FOV 302. The virtual 3D objects 304A, 304B can be translated within the same vertical plane until convergence. The virtual 3D objects 304A, 304B can have a starting point within the user's FOV 302 equidistant within the same vertical plane from a mid-point of the FOV. Utilizing application software, the virtual 3D objects 304A, 304B are translated and projected on the combiner lenses 104A, 104B to give the appearance that the virtual 3D objects are a set distance from the view of the user's eyes 106A, 106B. The application software can present the virtual 3D objects 304A, 304B via the combiner lenses 104A, 104B so that the virtual 3D objects can appear to be at different distances from the user's eyes 106A, 106B. In some embodiments the presentation of the virtual 3D objects 304A, 304B can correspond to projection of the virtual 3D objects at distances of 16 inches to 20 feet in front of the user's eyes 106A, 106B. The range of distances allow phoria to be measured at different intervals of depth for better confidence in convergence results. As the virtual 3D objects 304A, 304B approach the mid-point of the user's FOV 302, the user can provide input to the application software or platform software. The input can take the form of voice commands, gestures, or input from a "clicker." As the virtual 3D objects 304A, 304B approach each other, they will begin to overlap and converge into a single visible virtual 3D object. At the point in which the convergence becomes clear to the user, the user can provide input to stop any motion or translation of the virtual 3D objects 304A, 304B. The application software evaluates a delta between the midpoint of the user's FOV 302 and the point at which the virtual 3D objects 304A, 304B were located when the user provided input to stop the motion or translation. As mentioned above, the delta can be represented as a deviation relative to the virtual distance of the virtual 3D objects 304A, 304B from the patient. A diopter is measured by the deviation of the image at a specific virtual distance (1 prism diopter=1 virtual centimeter deviation of the image at a 1 virtual meter distance).

Figure 4A:
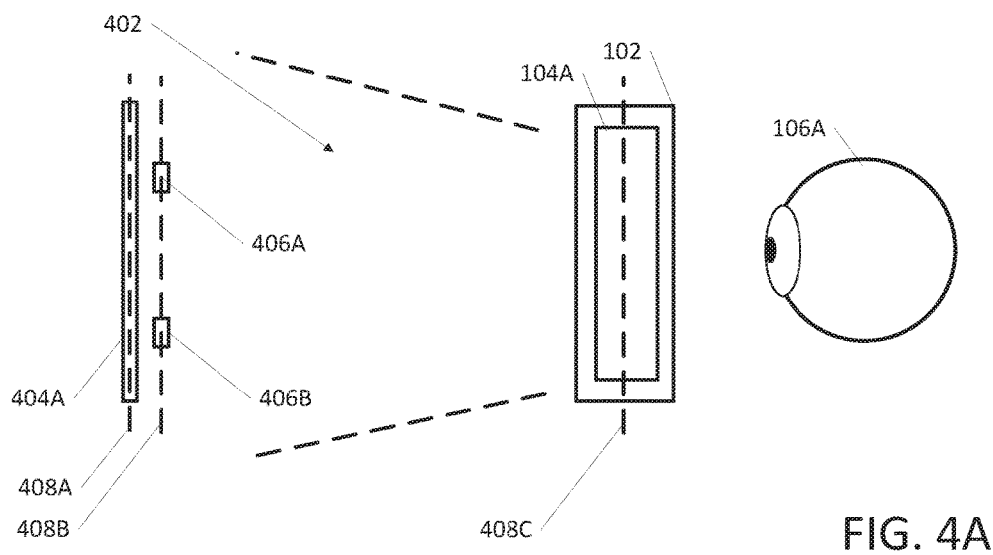
FIG. 4A is a block diagram illustrating a test for astigmatism utilizing the holographic refraction eye testing device according to an exemplary embodiment.

FIG. 4A is a block diagram illustrating a test for astigmatism utilizing the holographic refraction eye testing device according to an exemplary embodiment. In one embodiment, multiple virtual 3D objects 404A, 406A, 406B can be manipulated in a user's FOV 402. The virtual 3D objects 404A, 406A, 406B start in different planes 408A, 408B parallel to the plane of the combiner lenses 408C. In one embodiment, the virtual 3D objects 404A can be a set of vertical lines (relative to the user's eyes 106A, 106B) residing in a plane 408A. Additional virtual 3D objects 406A, 406B can be a set of horizontal lines (relative to the user's eyes 106A, 106B) residing in a plane 408B. When viewed through the combiner lenses 104A, 104B in the FOV 402, the virtual 3D objects 404A, 406A, 406B can appear as a hash mark (#) where the virtual 3D objects appear to intersect, however since they are in different planes 408A, 408B they do not actually intersect.

In one embodiment, the user can start the test by providing input to the computing system 108. The input can take the form of voice commands, including saying key words indicative of beginning the test, gestures or providing input from a "clicker." In one embodiment, the user states the word "start" to begin the test. Control of the test can take the form voice commands including "forward" and "backward." A voice command of "forward" translates the plane 408A, and associated virtual 3D objects 404A toward the combiner lenses 104A, 104B. A voice command of "backward" translates the plane 408A, and associated virtual 3D objects 404A away from the combiner lenses 104A, 104B. Utilizing the voice commands and associated translations, a user can manipulated the virtual 3D objects 404A where the user believes the respective planes 408A, 408B and associated virtual 3D objects 404A, 406A, 406B are coincidental. The user can provide a voice command to the computing system 108, such as stating the word "stop" to complete the manipulation portion of the test. Upon the receipt of the "stop" command, the computing system 108 disallows subsequent input commands, such as "forward" and "backward," and determines a delta distance between the final location of the planes 408A, 408B. In the event the user manipulated the planes 408A, 408B to coincide, the delta would be zero.

Figure 4B:
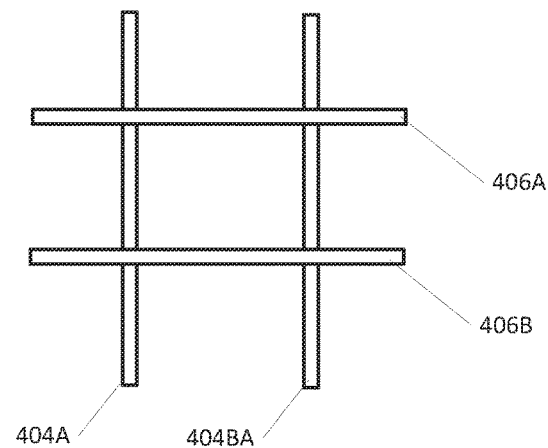
FIG. 4B is a block diagram illustrating a user's perspective of the virtual 3D objects depicted in FIG. 4A according to an exemplary embodiment.

FIG. 4B is a block diagram illustrating a user's perspective of the virtual 3D objects depicted in FIG. 4A. Virtual 3D objects 406A, 406B can be implemented as parallel lines residing the same plane 408B. Virtual 3D objects 404A, 404B can be implemented as parallel lines residing in the same plane 408A.

Figure 5A:
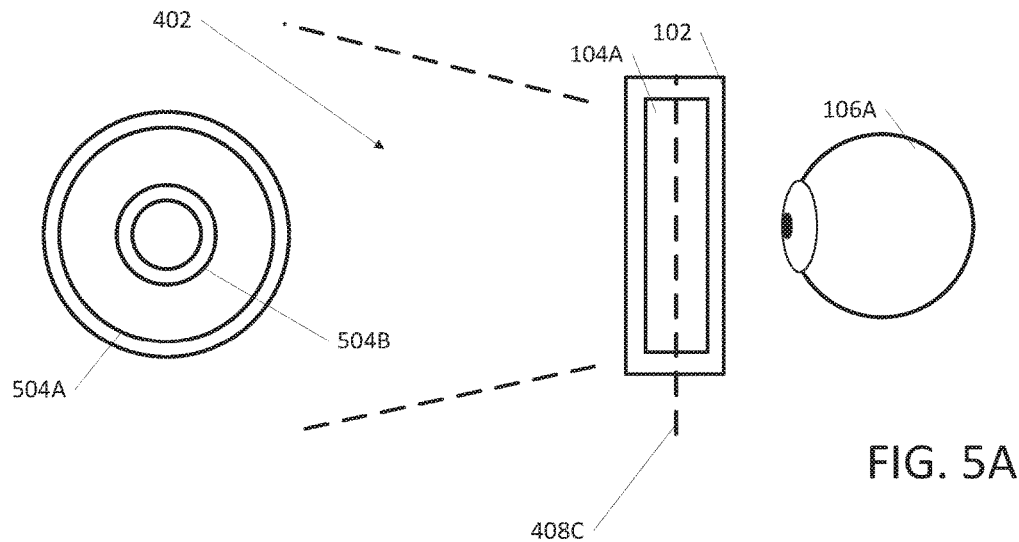
FIG. 5A is a block diagram illustrating a test for astigmatism utilizing the holographic refraction eye testing device according to an exemplary embodiment.
Figure 5B:
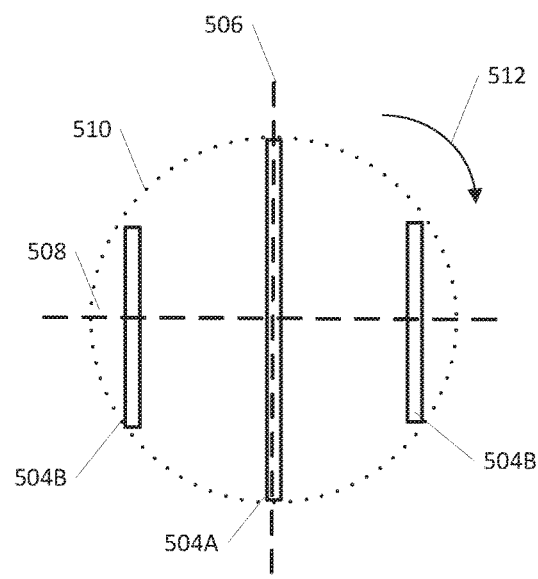
FIG. 5B is a block diagram illustrating a user's perspective of the virtual 3D objects depicted in FIG. 5A according to an exemplary embodiment.

FIG. 5A is a block diagram illustrating a test for astigmatism utilizing the holographic refraction eye testing device according to an exemplary embodiment. FIG. 5B is a block diagram illustrating a user's perspective of the virtual 3D objects depicted in FIG. 5A. In one embodiment, multiple virtual 3D objects 504A, 504B can be manipulated in a user's FOV 402. The virtual 3D objects 504A, 504B correspond to concentric opaque rings across the surface of an invisible sphere 510, where the concentric opaque rings traverse the surface of the sphere perpendicular to the plane of the combiner lenses 104A, 104B. The virtual 3D objects 504A, 504B can be oriented along coaxial planes 506, 508. In other embodiments, the virtual 3D objects 504A, 504B can be distal or proximal portions of concentric opaque rings across the surface of an invisible sphere 510.

In one embodiment, the user can start the test by providing input to the computing system 108. The input can take the form of voice commands, including saying key words indicative of beginning the test, gestures or providing input from a "clicker." The user states the word "start" to begin the test. As the test begins the invisible sphere 510 and accompanying virtual 3D objects are translated toward the combiner lenses 104A, 104B to give the user the appearance that the virtual 3D objects are coming directly at the user's eyes 106A. When the user can see the virtual 3D objects 504A, 504B clearly, the user can provide input to stop the test in the form of a voice command of "stop." The computing system 108 ceases translation of the invisible sphere 510 and calculates a delta distance from the starting point of the invisible sphere to the point where the invisible sphere resides at the end of the test. A constant point of reference on the invisible sphere 510 can be utilized to determine a consistent location to determine the delta distance.

In another embodiment, the user can start the test by providing input to the computing system 108. The input can take the form of voice commands, including saying key words indicative of beginning the test, gestures or providing input from a "clicker." The user states the word "start" to begin the test. The virtual 3D objects 504A, 504B being the test in a parallel or coincidental plane with a starting plane 506. As the test begins the invisible sphere 510 and accompanying virtual 3D objects are rotated in a clockwise motion 512 from the user's perspective. When the invisible sphere 510 and accompanying virtual 3D objects appear to have rotated ninety (90) degrees from the original starting position, (parallel or coincidental to the horizontal plane 508), the user can provide input to stop the test in the form of a voice command of "stop." The computing system 108 ceases rotation of the invisible sphere 510 and calculates a delta in degrees based on the rotation from the starting point of the invisible sphere to the orientation of the invisible sphere at the end of the test. The delta in degrees can be used to determine the axis of the astigmatism. This will provide the amount of astigmatism measured in this eye and therefore the predicted amount of cylindrical correction needed to bring clarity.

Figure 5C:
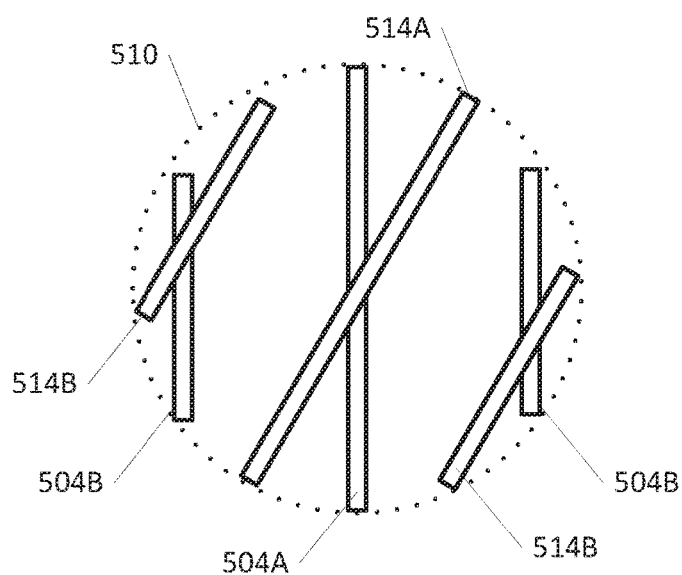
FIG. 5C is a block diagram illustrating another perspective of the virtual 3D objects depicted in FIG. 5A according to an exemplary embodiment.

FIG. 5C is a block diagram illustrating another user's perspective of the virtual 3D objects depicted in FIG. 5A. In another embodiment, the virtual 3D objects 504A, 504B can be distal portions of concentric opaque rings across the surface of an invisible sphere 510. The virtual 3D objects 514A, 514B can be proximal portions of concentric opaque rings across the surface of an invisible sphere 510. The distal portions of the concentric opaque rings form a group and the proximal portions form a group. Groups are rotated and translated in the FOV 402 in unison. The distal portions can be offset from the proximal portions by a rotation of 45 degrees. The user can start the test by providing input to the computing system 108. The input can take the form of voice commands, including saying key words indicative of beginning the test, gestures or providing input from a "clicker." The user states the word "start" to begin the test. The computing system 108 translates virtual 3D objects 514A, 514B corresponding to the proximal portions toward the combiner lenses 104A, 104B where the virtual 3D object 514A, 514B appear to be coming toward the user's eyes 102A, 102B. When the user determines that the virtual 3D objects 514A, 514B are clear and distinct from the distal virtual 3D objects 504A, 504B, the user can provide input to stop the test in the form of a voice command of "stop." The computing system 108 ceases translation of the virtual 3D objects 514A, 514B corresponding to the proximal portions and calculates a delta in distance based on the translation from the starting point to the position at the end of the test.

Figure 6:
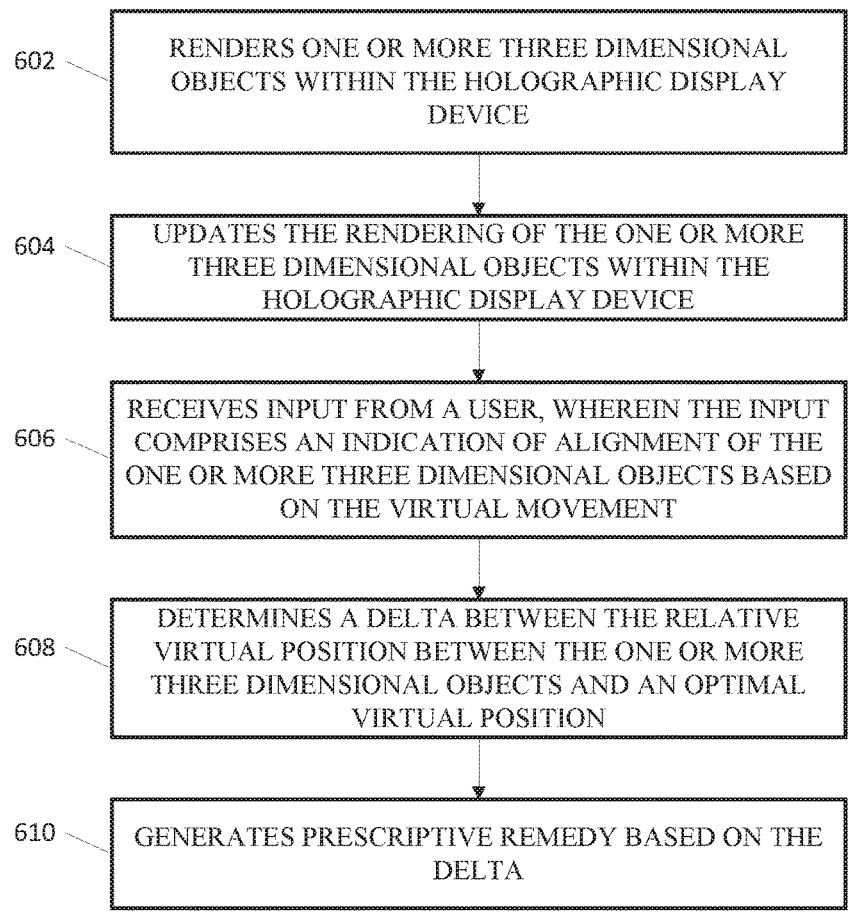
FIG. 6 depicts a block diagram an exemplary computing device in accordance with an exemplary embodiment.

FIG. 6 depicts a block diagram an exemplary computing device in accordance with an exemplary embodiment.

At step 602, the holographic display device renders one or more three dimensional objects with the holographic display device. The rendering corresponds to a virtual level of depth viewable by a user.

At step 604, the holographic display device updates the rendering of the one or more three dimensional objects within the holographic display device. The updated rendering includes a virtual movement of the one or more three dimensional objects within the virtual level of depth. The virtual movement includes moving the one or more three dimensional objects laterally in the field of view of the user. Alternatively, the virtual movement includes moving the one or more three dimensional objects vertically in the field of view of the user. Additionally, the virtual movement includes moving the one or more three dimensional objects from a distal position to proximal position within the field of view of the user. The virtual level of depth corresponds to a simulated distance away from the user. The simulated distance can range from sixteen (16) inches to twenty (20) feet from the user.

At step 606, the holographic display device receives input from a user. The input can include an indication of alignment of the one or more three dimensional objects based on the virtual movement. The indication of alignment can include a relative virtual position between the one or more three dimensional objects. The input from the user can include hand gestures and voice commands At step 608, the holographic display device determines a delta between the relative virtual position of the one or more three dimensional objects and an optimal virtual position.

At step 610, the holographic display device generates a prescriptive remedy based on the delta between the relative virtual position of the one or more three dimensional objects and the optimal virtual position.

Figure 7:
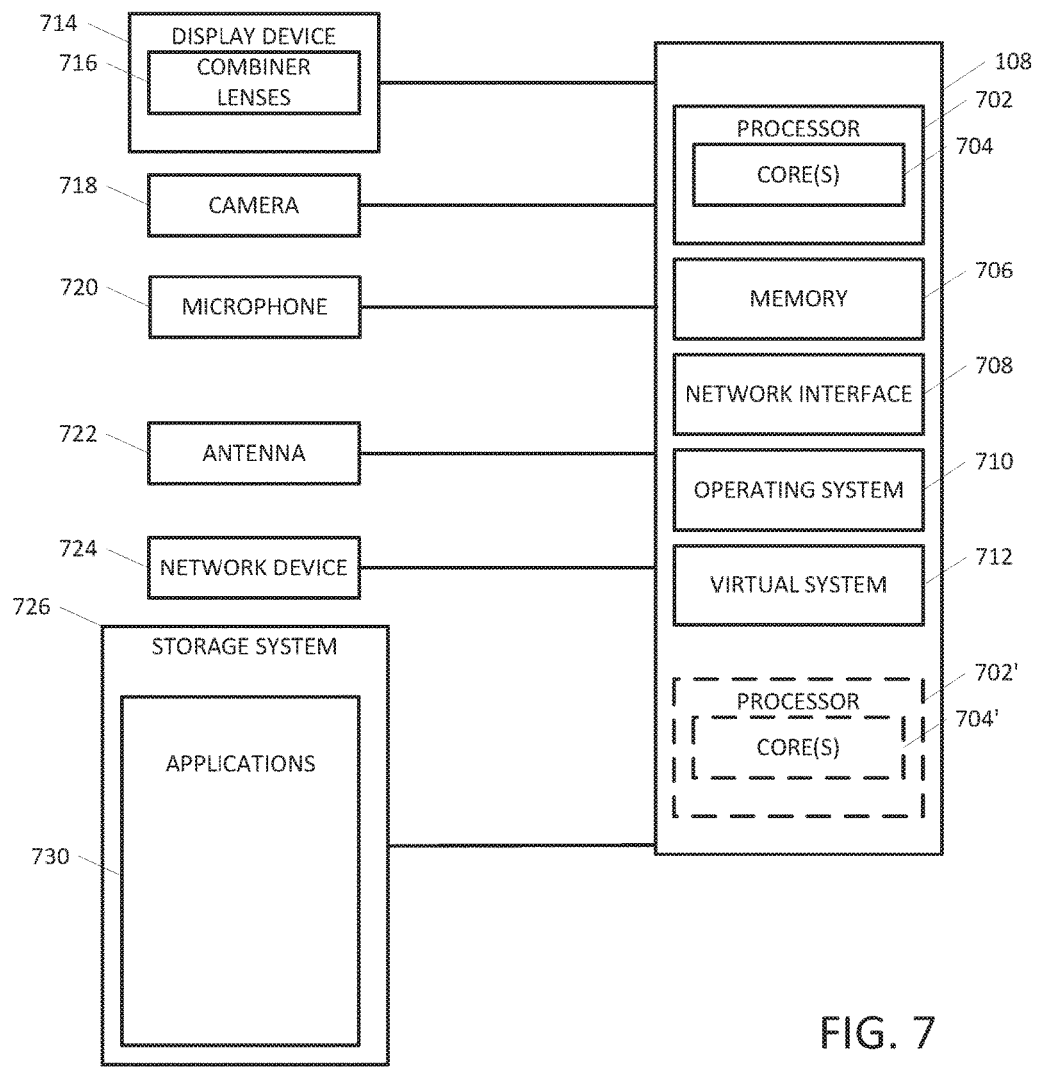
FIG. 7 is a block diagram illustrating a process for utilizing the holographic refraction eye testing device according to an exemplary embodiment.

FIG. 7 depicts a block diagram an exemplary computing device in accordance with an exemplary embodiment. Embodiments of the computing device 700 can implement embodiments of the system including the holographic refraction eye testing device. For example, the computing device can be embodied as a portion of the holographic refraction eye testing device, and supporting computing devices. The computing device 700 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more flash drives, one or more solid state disks), and the like. For example, memory 706 included in the computing system 108 may store computer-readable and computer-executable instructions or software (e.g., applications 730 such as rendering application) for implementing exemplary operations of the computing device 700. The computing system 108 also includes configurable and/or programmable processor 702 and associated core(s) 704, and optionally, one or more additional configurable and/or programmable processor(s) 702' and associated core(s) 704' (for example, in the case of computer systems having multiple processors/cores), for executing computer-readable and computer-executable instructions or software stored in the memory 706 and other programs for implementing exemplary embodiments of the present disclosure. Processor 702 and processor(s) 702' may each be a single core processor or multiple core (704 and 704') processor. Either or both of processor 702 and processor(s) 702' may be configured to execute one or more of the instructions described in connection with computing system 108.

Virtualization may be employed in the computing system 108 so that infrastructure and resources in the computing system 108 may be shared dynamically. A virtual machine 712 may be provided to handle a process running on multiple processors so that the process appears to be using only one computing resource rather than multiple computing resources. Multiple virtual machines may also be used with one processor.

Memory 706 may include a computer system memory or random access memory, such as DRAM, SRAM, EDO RAM, and the like. Memory 706 may include other types of memory as well, or combinations thereof. The computing system 108 can receive data from input/output devices. A user may interact with the computing system 108 through a visual display device 714, such as a combiner lenses 716, which may display one or more virtual graphical user interfaces, a microphone 720 and one or more cameras 718.

The computing system 108 may also include one or more storage devices 726, such as a hard-drive, CD-ROM, or other computer readable media, for storing data and computer-readable instructions and/or software that implement exemplary embodiments of the present disclosure. For example, exemplary storage device 726 can include storing information associated with platform software and the application software.

The computing system 108 can include a network interface 708 configured to interface via one or more network devices 724 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. In exemplary embodiments, the computing system can include one or more antennas 722 to facilitate wireless communication (e.g., via the network interface) between the computing system 108 and a network and/or between the computing system 108 and other computing devices. The network interface 708 may include a built-in network adapter, network interface card, PCMCIA network card, card bus network adapter, wireless network adapter, USB network adapter, modem or any other device suitable for interfacing the computing system 108 to any type of network capable of communication and performing the operations described herein.

The computing system 108 may run any operating system 710, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, or any other operating system capable of running on the computing system 108 and performing the operations described herein. In exemplary embodiments, the operating system 710 may be run in native mode or emulated mode. In an exemplary embodiment, the operating system 710 may be run on one or more cloud machine instances.

In describing exemplary embodiments, specific terminology is used for the sake of clarity. For purposes of description, each specific term is intended to at least include all technical and functional equivalents that operate in a similar manner to accomplish a similar purpose. Additionally, in some instances where a particular exemplary embodiment includes multiple system elements, device components or method steps, those elements, components, or steps can be replaced with a single element, component, or step. Likewise, a single element, component, or step can be replaced with multiple elements, components, or steps that serve the same purpose. Moreover, while exemplary embodiments have been shown and described with references to particular embodiments thereof, those of ordinary skill in the art will understand that various substitutions and alterations in form and detail can be made therein without departing from the scope of the present disclosure. Further, still, other aspects, functions, and advantages are also within the scope of the present disclosure.

Exemplary flowcharts are provided herein for illustrative purposes and are non-limiting examples of methods. One of ordinary skill in the art will recognize that exemplary methods can include more or fewer steps than those illustrated in the exemplary flowcharts and that the steps in the exemplary flowcharts can be performed in a different order than the order shown in the illustrative flowcharts.

We claim:

1. An apparatus for diagnosis and prescription of remedies for visual impairment, comprising:
    a head mounted holographic display device;
    a computing device communicatively coupled to the head mounted holographic display device;
    a diagnostic module configured to execute on the computing device, the diagnostic module when executed:
        renders one or more three dimensional objects within the holographic display device, wherein the rendering corresponds to a virtual level of depth viewable by a user;
        updates the rendering of the one or more three dimensional objects within the holographic display device, wherein the updates comprise a virtual movement of the one or more three dimensional objects within the virtual level of depth;
        receives input from a user, wherein the input comprises an indication of alignment of the one or more three dimensional objects based on the virtual movement, wherein the indication of alignment comprises a relative virtual position between the one or more three dimensional objects;
        determines a delta between the relative virtual position of the one or more three dimensional objects and an optimal virtual position; and
        generates prescriptive remedy based on the delta between the relative virtual position of the one or more three dimensional objects and the optimal virtual position.

2. The system of claim 1, wherein the virtual movement comprises moving the one or more three dimensional objects laterally in the field of view of the user.

3. The system of claim 1, wherein the virtual movement comprises moving the one or more three dimensional objects vertically in the field of view of the user.

4. The system of claim 1, wherein the virtual movement comprises moving the one or more three dimensional objects from a distal position to proximal position within the field of view of the user.

5. The system of claim 1, wherein the virtual level of depth corresponds to a simulated distance away from the user.

6. The system of claim 1, wherein the input from the user comprises hand gestures and voice commands.

7. The system of claim 1, wherein the head mounted display device comprises a pair of transparent combiner lenses calibrated to the interpupillary distance.

8. A method for diagnosis and prescription of remedies for visual impairment, comprising:
    rendering, on a head mounted holographic display device, one or more three dimensional objects within the holographic display device, wherein the rendering corresponds to a virtual level of depth viewable by a user;
    updating, the rendering of the one or more three dimensional objects within the holographic display device, wherein the updates comprise a virtual movement of the one or more three dimensional objects within the virtual level of depth;

receiving, input from a user, wherein the input comprises an indication of alignment of the one or more three dimensional objects based on the virtual movement, wherein the indication of alignment comprises a relative virtual position between the one or more three dimensional objects;

determining, a delta between the relative virtual position of the one or more three dimensional objects and an optimal virtual position; and generating prescriptive remedy based on the delta between the relative virtual position of the one or more three dimensional objects and an optimal virtual position.

9. The method of claim 8, wherein the virtual movement comprises moving the one or more three dimensional objects laterally in the field of view of the user.

10. The method of claim 8, wherein the virtual movement comprises moving the one or more three dimensional objects vertically in the field of view of the user.

11. The method of claim 8, wherein the virtual movement comprises moving the one or more three dimensional objects from a distal position to proximal position within the field of view of the user.

12. The method of claim 8, wherein the virtual level of depth corresponds to a simulated distance away from the user.

13. The method of claim 8, wherein the input from the user comprises hand gestures and voice commands.

14. The method of claim 8, wherein the head mounted display device comprises a pair of transparent combiner lenses calibrated to the interpupillary distance.

15. A non-transitory computer readable medium for the diagnosis and prescription of remedies for visual impairments, having stored thereon, instructions that when executed in a computing system, cause the computing system to perform operations comprising:

rendering, on a head mounted holographic display device, one or more three dimensional objects within the holographic display device, wherein the rendering corresponds to a virtual level of depth viewable by a user;

updating, the rendering of the one or more three dimensional objects within the holographic display device, wherein the updates comprise a virtual movement of the one or more three dimensional objects within the virtual level of depth;

receiving, input from a user, wherein the input comprises an indication of alignment of the one or more three dimensional objects based on the virtual movement, wherein the indication of alignment comprises a relative virtual position between the one or more three dimensional objects;

determining, a delta between the relative virtual position between the one or more three dimensional objects and an optimal virtual position; and generating prescriptive remedy based on the delta.

16. The computer readable medium of claim 15, wherein the virtual movement comprises moving the one or more three dimensional objects laterally in the field of view of the user.

17. The computer readable medium of claim 15, wherein the virtual movement comprises moving the one or more three dimensional objects vertically in the field of view of the user.

18. The computer readable medium of claim 15, wherein the virtual movement comprises moving the one or more three dimensional objects from a distal position to proximal position within the field of view of the user.

19. The computer readable medium of claim 15, wherein the virtual level of depth corresponds to a simulated distance away from the user.

20. The computer readable medium of claim 15, wherein the head mounted display device comprises a pair of transparent combiner lenses calibrated to the interpupillary distance.

* * * * *